United States Patent [19]

Parker et al.

[11] Patent Number: 4,554,128

[45] Date of Patent: Nov. 19, 1985

[54] NUCLEAR FUEL ROD END PLUG WELD INSPECTION

[75] Inventors: Merle A. Parker; George F. Rice; Stanley S. Patrick, all of Columbia, S.C.

[73] Assignee: Westinghouse Electric Corp., Pittsburgh, Pa.

[21] Appl. No.: 470,906

[22] Filed: Mar. 1, 1983

[51] Int. Cl.⁴ .................................................. G21C 17/00
[52] U.S. Cl. ...................................... 376/252; 376/251; 378/45
[58] Field of Search ............................... 376/251, 252; 378/44–49

[56] References Cited

PUBLICATIONS

"Ultrasonic Testing of Materials", Krautkramer et al, N.Y., Springer Verlag Berlin Heidelberg (1977), 2nd Ed. pp. 429, 431–432, 440, 444, 448, 451–468, 492.
"Ultrasonic Flow Detection in Metals", N. J. Banks et al, Prentice Hall, Inc., 1962, pp. 112–113, 119, 142, 156–157, 194–195, 199, 233.
Proc. 9th Conf. Appl. X-Ray Analysis, "Advance in X-Ray Analysis", vol. 4, Stever et al (8/50), pp. 474–475.
Welding Handbook, 7th Ed., vol. 2, Kearns, (1978), pp. 78, 81 110–111.

*Primary Examiner*—Sal Cangialosi
*Attorney, Agent, or Firm*—D. E. Erickson

[57] ABSTRACT

Apparatus and method for testing TIG (tungsten inert gas) welds of end plugs on a sealed nuclear reactor fuel rod. An X-ray fluorescent spectrograph testing unit detects tungsten inclusion weld defects in the top end plug's seal weld. Separate ultrasonic weld inspection system testing units test the top end plug's seal and girth welds and test the bottom end plug's girth weld for penetration, porosity and wall thinning defects. The nuclear fuel rod is automatically moved into and out from each testing unit and is automatically transported between the testing units by rod handling devices. A controller supervises the operation of the testing units and the rod handling devices.

8 Claims, 5 Drawing Figures

NUCLEAR FUEL ROD END PLUG WELD INSPECTION

BACKGROUND OF THE INVENTION

The present invention relates generally to quality control inspection of nuclear reactor fuel rods, and more particularly, to an apparatus and method for inspecting TIG (tungsten inert gas) welds of an end plug on a sealed fuel rod.

A typical nuclear fuel rod includes an elongated cladding tube containing nuclear fuel pellets, a bottom end plug girth welded to the bottom of the cladding tube, and a top end plug girth welded to the top of the cladding tube. The top end plug usually contains an axial bore through which the interior of the cladding tube is pressurized with a gas (such as helium). The axial bore is then closed with a seal weld. The girth and seal welds are typically TIG welds. Quality control inspection of the manufactured fuel rod has included inspection of the top end plug's girth and seal welds, and the bottom end plug's girth weld.

In a conventional X-ray weld inspection technique, an X-ray film was developed for a weld area and was subjectively evaluated by an inspector. Relatively heavy shielding was required to minimize radiation exposure to personnel. The X-ray system detected tungsten inclusions in the top end plug's seal weld. Since the seal weld was made under pressure, a higher potential was required for the welding electrode to overcome the dielectric of the pressurized gas, and tungsten from the TIG welding tip could be ejected into the weldment. Tungsten inclusions were less of a problem with the unpressurized girth welds. The X-ray system also detected voids in the girth and seal welds. By a "void" is meant an area devoid of weldment which should have such weldment. It includes a cavity within a weldment as well as a weldment which is lacking in desired thickness.

Conventional ultrasonic flaw detection techniques have been applied to material and weld inspection, typically in non-nuclear fuel rod areas. Existing ultrasonic inspection systems have included the use of multiple transducers for better void detection, the capability of automatic testing, and the use of flaw alarm monitors. Pipes have been tested in transit tanks according to the immersion technique, with spiral translatory motion of the pipes. The entrance and exit openings of the tank were sealed in such a way that, during the test run, the pipes remained submerged to a sufficient depth. Canning tubes for nuclear reactor fuel elements have been tested by the immersion method using a long tank with completely immersed pipes and traveling probes, or using a transit tank through which the pipe is fed in spiral motion, with the probes remaining stationary. Ultrasonic weld inspection systems detect the material/air boundary of voids (either the thin wall or cavity type), but cannot reliably detect tungsten inclusions (which give a material/material boundary) which can arise from TIG seal welding. The presence of a precalculated amount of tungsten is a weld defect which must be tested for by any nuclear fuel rod end plug weld inspection apparatus.

SUMMARY OF THE INVENTION

Briefly stated, the invention is directed towards apparatus for inspecting end plug TIG welds on a sealed nuclear fuel rod. The apparatus includes an X-ray fluorescent spectrograph to detect tungsten in the welds and an ultrasonic weld inspection system to detect voids in the welds. There also are devices for moving the end plug into and out from the X-ray fluorescent spectrograph, into and out from the ultrasonic weld inspection system, and between the X-ray fluorescent spectrograph and the ultrasonic weld inspection system. A controller regulates (in a predetermined manner) the three end plug moving devices, the X-ray fluorescent spectrograph, and the ultrasonic weld inspection system.

The invention also is directed towards a second ultrasonic weld inspection system in combination with the apparatus described in the preceding paragraph in which the second ultrasonic weld inspection system tests the girth weld of the bottom end plug for voids, the X-ray fluorescent spectrograph tests the seal weld of the top end plug for tungsten, and the first ultrasonic weld inspection system tests the girth and seal welds of the top end plug for voids.

The invention additionally is directed towards a method for inspecting end plug TIG welds on a sealed nuclear fuel rod which includes testing the welds for voids with an ultrasonic weld inspection system and testing the welds for tungsten with an X-ray fluorescent spectrograph.

BRIEF DESCRIPTION OF THE DRAWINGS

The subject matter of the invention is particularly pointed out and distinctly claimed in the concluding portion of this specification. The invention, however, both as to organization and method operation, together with further advantages thereof, may best be understood by reference to the following description taken in connection with the accompanying drawings in which:

DETAILED DESCRIPTION OF THE INVENTION

Figure 1:
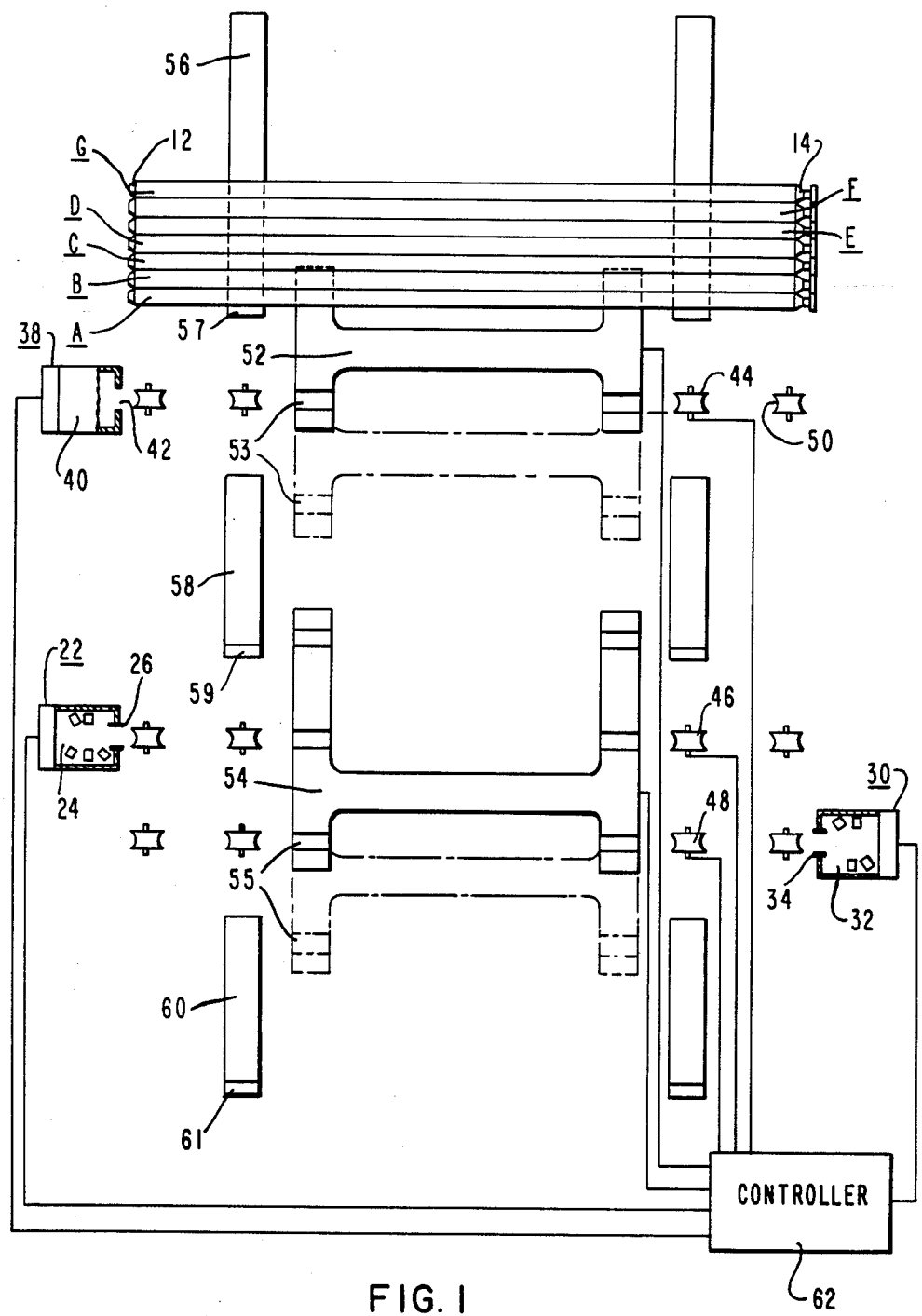
FIG. 1 is a planar schematic view of an embodiment of the invention with several fuel rods about to enter the end plug weld inspection line.

Referring now to the drawings wherein like reference characters designate like or corresponding parts throughout the several views, there is shown in the figures apparatus for inspecting the TIG welds of the end plugs on sealed nuclear reactor fuel rods A, B, C, D, E, F and G.

The top end plug 12 has the composition of its seal weld 18 tested for tungsten inclusions by an X-ray fluorescent spectrograph 38. The X-ray fluorescent spectrograph 38 has been calibrated, as is known to those skilled in the art, the detect tungsten. Basically, an X-ray fluorescent spectrograph directs a beam of primary radiation onto the surface of the seal weld 18. This radiation causes the seal weld 18 to emit secondary radiation which contains characteristic lines of each element present in the weld. The characteristic radiation from all elements of the weld is directed through a collimator into a variable goniometer assembly which contains a single crystal and detector. The crystal acts as a diffraction grating which separates the various wavelengths emitted by the different elements. By setting the goniometer assembly at a specific angle, the peak response from tungsten is detected and evaluated. A shielded counting chamber 40 of the X-ray fluorescent spectrograph has a suitably sized orifice 42 for receiving the top end plug 12. The more tungsten present in the seal weld 18, the more secondary radiation counts in a given time are detected by the X-ray fluorescent spectrograph. Counts exceeding a pre-calculated value indicate the fuel rod should be rejected for having a defective seal weld.

The top end plug 18 has the integrity of its girth weld 16 and its seal weld 18 tested for voids (i.e. empty space due to cavities within the weldment, or empty space due to the weldment lacking the proper thickness) by a first multiple transducer ultrasonic weld inspection system 22 modified for testing nuclear fuel rod end plugs. Modifications include disposing the multiple ultrasonic transducers 28 in an immersion tank stuffing box 24 which has a seal (such as a gland seal 26) for receiving the top end plug 12 to have its girth weld 16 and seal weld 18 interrogated by the transducers 28. The ultrasonic system 22 employs standard rod rotational plus translational movement to ensure full weld coverage. The orientation and gain of the transducers 28 are set, as is known to those skilled in the art, to detect weld voids exceeding a preselected value by using test welds containing holes of known size or natural defects. It has been found that adequate testing of the top end plug 12 requires five transducers 28: four for the girth weld 16 and one for the seal weld 18. Basically, an ultrasonic inspection system uses a transducer to transmit an ultrasonic signal and, by proper gating, to detect a reflected or return signal from the area of interrogation indicating a discontinuity. The most easily and reliably detected weld discontinuities are voids in the weldment area (i.e. cavities within the weldment, or the empty space on the other side of a thin weldment). The magnitude of the reflected signal depends on the extent of the void. Ultrasonic inspection systems include standard alarm circuits which trigger when a reflected signal is detected which exceeds a preselected magnitude indicating, in the case of the present invention, that the fuel rod should be rejected for having a defective seal and-/or girth weld.

The bottom end plug 14 has the integrity of its girth weld 20 tested for voids by a second ultrasonic weld inspection system 30, generally identical to, and with the same modifications as, the previously described first ultrasonic weld inspection system 22. It has been found that four transducers 36 are required for the second immersion tank stuffing box 32 to interrogate the girth weld 20 on the bottom end plug 14 which is received through the second gland seal 34.

Means are provided for axially moving the top end plug 12 into and out from the counting chamber 40; means are provided for longitudinally moving the top end plug 12 into and out from the first immersion tank stuffing box 24; and means are provided for lengthwise moving the bottom end plug 14 into and out from the second immersion tank stuffing box 32. Preferably, such means are generally identical and include three groups of driven rollers 44, 46 and 48. Each of the rollers 44, 46 and 48 has a circumferential channel or groove 50 disposed to receive the fuel rods (e.g. see FIG. 2 where fuel rod B is positioned on rollers 44). The rollers could be driven by motors either directly or through a chain drive or the like. Other such means includes a moving tray, a conveyor belt or any standard rod handling device.

Means are furnished for transporting the fuel rods A, B, C, D, E, F and G between the first stuffing box 24, the counting chamber 40, and the second stuffing box 32. Preferably, such means includes a walking beam. In a preferred arrangement, the groups of rollers 44, 46 and 48 are parallel, and two walking beams are used to carry the fuel rods A, B, C, D, E, F and G between the channels or grooves 50 of the groups of rollers 44, 46 and 48. The parallel groups of rollers 44, 46 and 48 (with their associated X-ray fluorescent spectrograph 38, first ultrasonic weld inspection system 22, and second ultrasonic weld inspection system 30, respectively) may be arranged so that the fuel rods A, B, C, D, E, F and G are tested in any order. The embodiment of the invention shown in the figures is arranged to arbitrarily first use the X-ray fluorescent spectrograph 38 to test the top end plug 22 seal weld 18 for tungsten, then use the first ultrasonic weld inspection system 22 to test the top end plug 12 seal 18 and girth 16 welds for voids, and finally use the second ultrasonic weld inspection system 30 to test the bottom end plug 14 girth 20 weld for voids.

Figure 2:
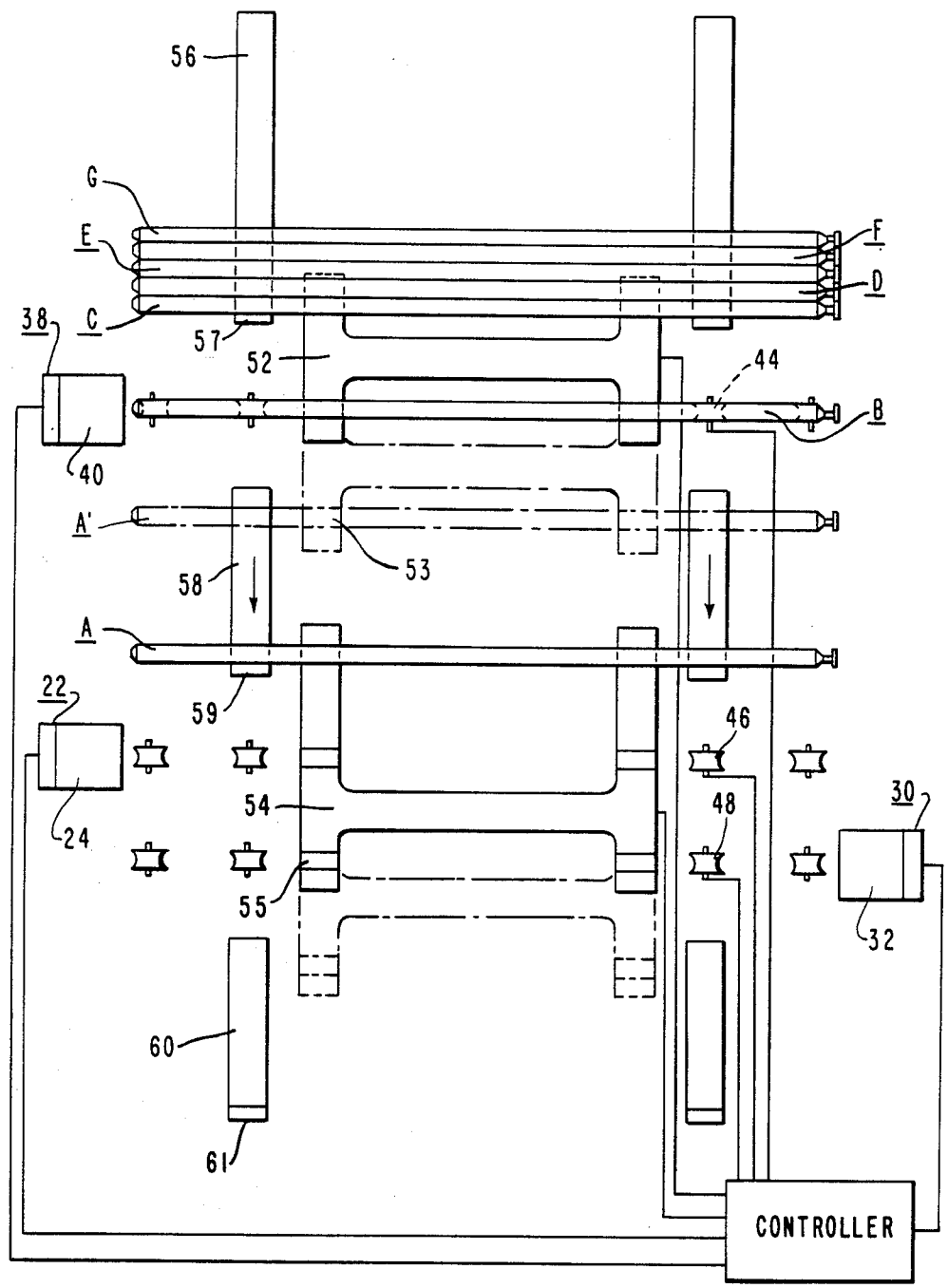
FIG. 2 is a view of FIG. 1 with some fuel rods having reached the X-ray fluorescent spectrograph station.
Figure 3:
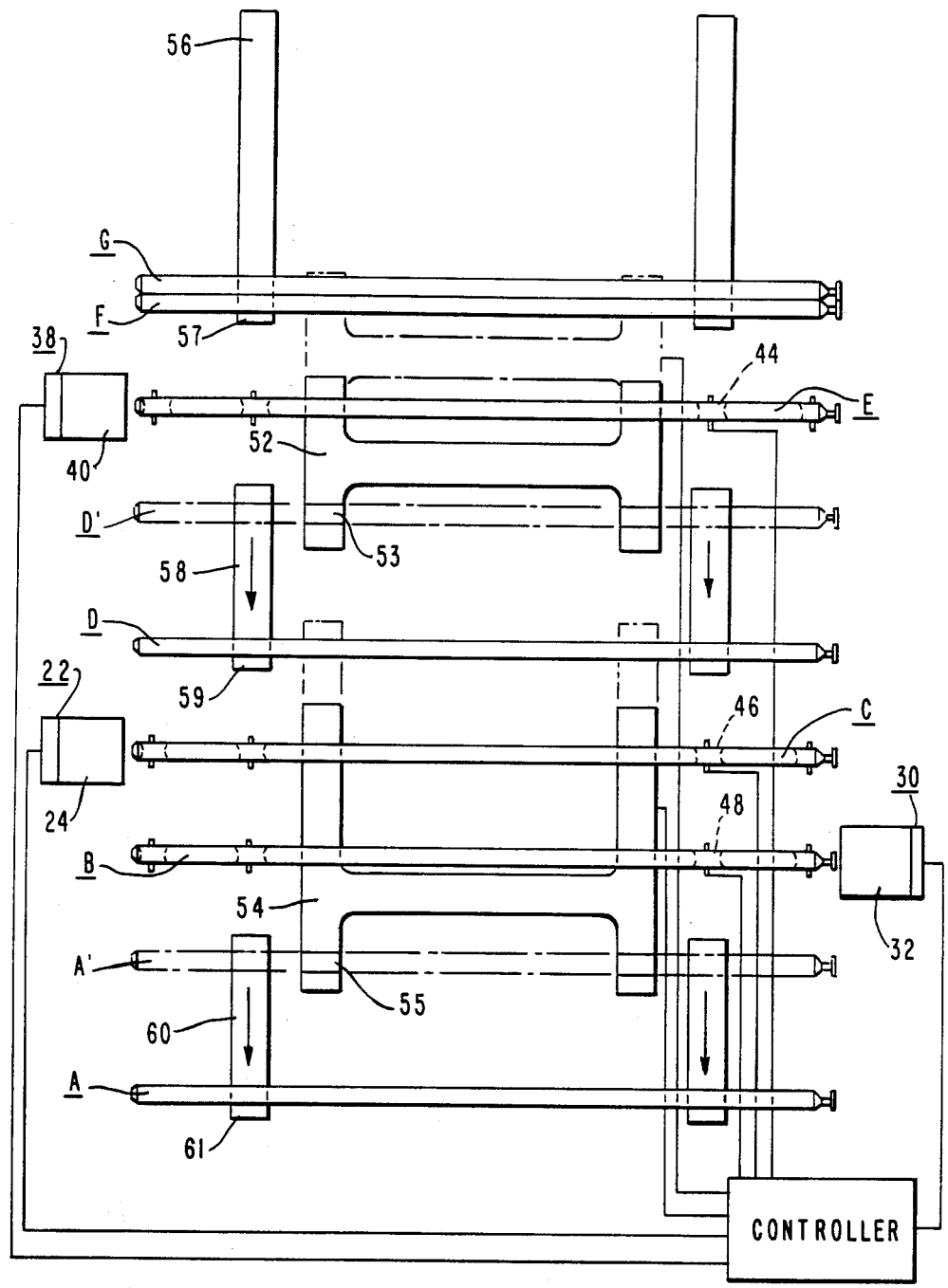
FIG. 3 is a view of FIG. 2 with some fuel rods also having reached the ultrasonic weld inspection system stations.
Figure 4:
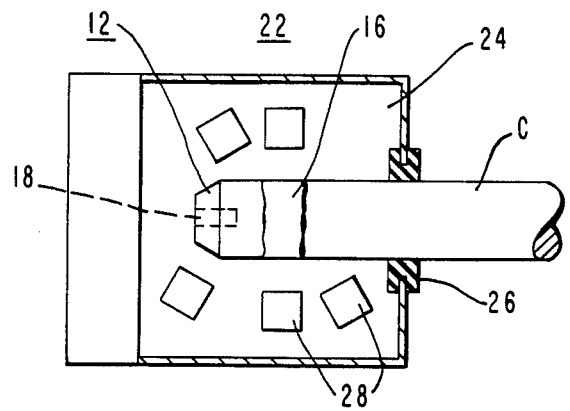
FIG. 4 is an enlarged schematic view of the top end plug's ultrasonic weld inspection system station.
Figure 5:
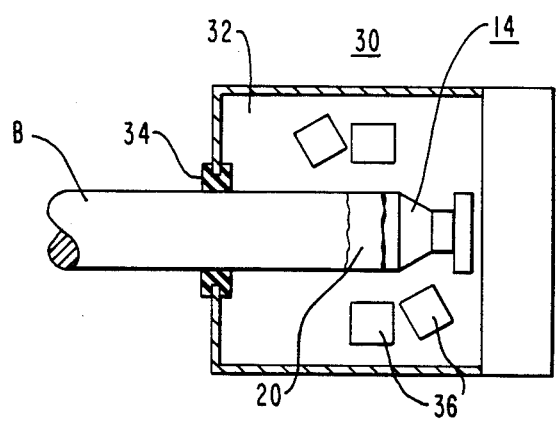
FIG. 5 is a similar view of FIG. 4 but of the bottom end plug's ultrasonic weld inspection system station.

In the preferred fuel rod transporting means shown in FIG. 1, the fuel rods A, B, C, D, E, F and G are initially positioned on an inclined entrance ramp 56 and have rolled against the ramp stop 61. A first walking beam 52 transfers the fuel rods in its slots 53. Walking beam 52 transfers one fuel rod from the entrance ramp 56 to the rollers 44 at the same time it transfers another fuel rod from the rollers 44 to a transfer ramp 58. As shown in FIG. 2, walking beam 52 has transported fuel rod B from the entrance ramp 56 to the rollers 44 and has transported fuel rod A from the rollers 44 to the transfer ramp 58. Fuel rod A has rolled down the transfer ramp 58 from its placement position A' to a position against the ramp stop 59. A second walking beam 54 transfers the fuel rods in its slots 55. Walking beam 54 simultaneously transfers one fuel rod from the transfer ramp 58 to the rollers 46, another fuel rod from the rollers 46 to the rollers 48, and yet another fuel rod from the rollers 48 to an exit ramp 60. As shown in FIG. 3, walking beam 54 has simultaneously transported fuel rod C from the transfer ramp 58 to rollers 46, fuel rod B from rollers 46 to rollers 48, and fuel rod A from rollers 48 to the exit ramp 60 where it has rolled against a stop 61. Other such fuel rod transporting means includes conventional pick and place type rod handling devices.

Means are supplied for controlling, in a predetermined manner, the top end plug axial moving means, the X-ray fluorescent spectrograph 38, the fuel rod transporting means, the top end plug longitudinal moving means, the first ultrasonic weld inspection system 22, the bottom end plug lengthwise moving means, and the second ultrasonic weld inspection system 30. Preferably, such means includes a microprocessor controller 62 and associated peripheral equipment to interface with the components to be controlled, as is known to those skilled in the art. Other such means includes a centralized board for manual activation of switches with circuits leading to the actuators for the walking beams, the rollers, and the ultrasonic and X-ray fluorescent testing units.

Additionally, it is preferable that the controlling means include means for generating a first reject signal when the X-ray fluorescent spectrograph 38 detects tungsten in an amount exceeding a precalculated value. For example, the microprocessor controller 62 could monitor the previously described secondary radiation counts detected by the Xray fluorescent spectrograph 38 and issue a weld defect signal when the counts reach a pre-calculated value, as is known to those skilled in the art. Likewise, it is preferred that the controlling means include means for generating other reject signals when either of the two ultrasonic weld inspection systems 22 and 30 detect a weld void exceeding a preselected magnitude. For example, the microprocessor controller 62 could monitor, as is known to those skilled in the art, the previously discussed ultrasonic inspection system alarm circuits triggered by a detected void exceeding a preselected magnitude, and the controller could thereupon issue a weld defect signal.

From the above description of an embodiment of the appratus of the invention, it is seen that the invention may also be described as a method for determining the integrity and composition of TIG welds of an end plug on a sealed nuclear reactor fuel rod which includes testing the welds for voids with a multiple transducer ultrasonic weld inspection system unit and testing the welds for tungsten with an X-ray fluorescent spectrograph unit and, preferably, automatically positioning the fuel rod for testing in each unit and moving the fuel rod between the units.

A typical cycle of operation, as controlled by the microprocessor controller 62, would have a fuel rod transported from the entrance ramp 56 to rollers 44 by the first walking beam 52. The rollers 44 would move the fuel rod's top end plug 12 into the X-ray fluorescent spectrograph 38, the spectrograph 38 would test for tungsten, and the rollers 44 would move the fuel rod's top end plug 12 out from the spectrograph 38. Then, the first walking beam 52 would transport the fuel rod to the transfer ramp 58. Next, the second walking beam 54 would transport the fuel rod to the rollers 46. The rollers 46 would move the fuel rod's top end plug 12 into the first ultrasonic weld inspection system 22, that system 22 would test for voids, and the rollers would move the fuel rod's top end plug 12 out from that system 22. Then the second walking beam 54 would transport the rod to the rollers 48. The rollers 48 would move the fuel rod's bottom end plug 14 into the second ultrasonic weld inspection system 30, that system 30 would test for voids, and the rollers would move the fuel rod's bottom end plug 14 out from that system 30. Then the second walking beam 54 would transport the fuel rod to the exit ramp 60. As previously mentioned, the first walking beam 52 simultaneously transports a fuel rod from the entrance ramp 56 to the rollers 44 and transports another fuel rod from the rollers 44 to the transfer ramp 58. Likewise, the second walking beam 54 simultaneously transports one fuel rod from the transfer ramp 58 to the rollers 46, transports another fuel rod from the rollers 46 to the rollers 48, and transports yet another fuel rod from the rollers 48 to the exit ramp 60.

It will be apparent that many modifications and variations are possible in light of the above teachings. It, therefore, is to be understood that within the scope of the appended claims, the invention may be practiced other than as specifically described.

We claim:

1. Apparatus for determining the integrity and composition of TIG welds of an end plug on a sealed nuclear reactor fuel rod, comprising:
    (a) an ultrasonic weld inspection system for void detection with multiple transducers and having an immersion tank stuffing box with a seal for receiving said end plug on said fuel rod, said transducers disposed in said stuffing box to interrogate said welds of said end plug;
    (b) means for longitudinally moving said end plug into and out from said stuffing box;
    (c) an X-ray fluorescent spectrograph calibrated to detect tungsten and having a shielded counting chamber with an orifice for receiving said end plug on said fuel rod;
    (d) means for axially moving said end plug into and out from said counting chamber;
    (e) means for transporting said fuel rod between said stuffing box and said counting chamber; and
    (f) means for controlling, in a predetermined manner, said end plug axial moving means, said X-ray fluorescent spectrograph, said fuel rod transporting means, said end plug longitudinal moving means, and said ultrasonic weld inspection system.

2. The apparatus of claim 1, wherein said end plug longitudinal moving means includes a first group of driven rollers each having a circumferential groove disposed to receive said fuel rod, and said end plug axial moving means includes a second group of driven rollers each having a circumferential channel disposed to receive said fuel rod.

3. The apparatus of claim 2, wherein said two groups of rollers are parallel, and wherein said fuel rod transporting means includes a walking beam for carrying said fuel rod beween said grooves of said first group of rollers and said channels of said second group of rollers.

4. The apparatus of claim 1, wherein said fuel rod transporting means includes a walking beam.

5. The apparatus of claim 1, wherein said controlling means also includes means for generating a first reject signal when said X-ray fluorescent spectrograph detects tungsten in an amount exceeding a precalculated value.

6. The apparatus of claim 1, wherein said controlling means also includes means for generating a second reject signal when said ultrasonic weld inspection system detects a weld void exceeding a preselected magnitude.

7. The apparatus of claim 1, wherein said controlling means includes a microprocessor.

8. Apparatus for inspecting TIG girth and seal welds of a top end plug and a girth TIG weld of a bottom end plug, both end plugs on a sealed nuclear reactor fuel rod, said apparatus comprising:
    (a) a first ultrasonic weld inspection system for void detection with a first set of multiple transducers and having a first immersion tank stuffing box with a first gland seal for receiving said top end plug on said fuel rod, said first set of transducers disposed in said first stuffing box to interrogate said girth and seal welds of said top end plug;
    (b) means for longitudinally moving said top end plug into and out from said first stuffing box;
    (c) an X-ray fluorescent spectrograph calibrated to detect tungsten and having a shielded counting chamber with an orifice for receiving said top end plug on said fuel rod;
    (d) means for axially moving said top end plug into and out from said counting chamber;

(e) a second ultrasonic weld inspection system for void detection with a second set of multiple transducers and having a second immersion tank stuffing box with a second gland seal for receiving said bottom end plug on said fuel rod, said second set of transducers disposed in said stuffing box to interrogate said girth weld of said bottom end plug;

(f) means for lengthwise moving said bottom end plug into and out from said second stuffing box;

(g) means for transporting said fuel rod between said first stuffing box, said counting chamber, and said second stuffing box; and (h) means for controlling, in a predetermined manner, said top end plug axial moving means, said X-ray fluorescent spectrograph, said fuel rod transporting means, said top end plug longitudinal moving means, said first ultrasonic weld inspection system, said bottom end plug lengthwise moving means, and said second ultrasonic weld inspection system.

* * * * *